US012767691B2

(12) United States Patent
Llinas

(10) Patent No.: US 12,767,691 B2
(45) Date of Patent: Oct. 20, 2026

(54) MATERIALS AND METHODS FOR MAKING SEXUAL STAGE PLASMODIUM PARASITES

(71) Applicant: The Penn State Research Foundation, University Park, PA (US)

(72) Inventor: Manuel Llinas, College, PA (US)

(73) Assignee: The Penn State Research Foundation, University Park (PA)

( * ) Notice: Subject to any disclaimer, the term of this patent is extended or adjusted under 35 U.S.C. 154(b) by 515 days.

(21) Appl. No.: 18/018,230

(22) PCT Filed: Oct. 15, 2021

(86) PCT No.: PCT/US2021/055201
§ 371 (c)(1),
(2) Date: Jan. 26, 2023

(87) PCT Pub. No.: WO2022/086814
PCT Pub. Date: Apr. 28, 2022

(65) Prior Publication Data

US 2023/0287066 A1 Sep. 14, 2023

Related U.S. Application Data

(60) Provisional application No. 63/094,280, filed on Oct. 20, 2020.

(51) Int. Cl.
*C07K 14/445* (2006.01)
*C12N 1/10* (2026.01)
*C12N 9/22* (2006.01)
*C12N 15/11* (2006.01)
*C12N 15/90* (2006.01)

(52) U.S. Cl.
CPC .............. *C07K 14/445* (2013.01); *C12N 1/10* (2013.01); *C12N 9/22* (2013.01); *C12N 15/11* (2013.01); *C12N 15/902* (2013.01); *C12N 2310/20* (2017.05); *C12N 2800/80* (2013.01)

(58) Field of Classification Search
CPC .................................................... C07K 14/445
See application file for complete search history.

(56) References Cited

U.S. PATENT DOCUMENTS

2020/0283391 A1 9/2020 McLeod et al.

OTHER PUBLICATIONS

Bechtsi, Dafni P., and A. P. Waters. "Genomics and epigenetics of sexual commitment in Plasmodium." International Journal for Parasitology 47.7 (2017): 425-434. (Year: 2017).*

Avraham et al., "Insulator-like pairing elements regulate silencing and mutually exclusive expression in the malaria parasite Plasmodium falciparum," Proc. Natl. Acad. Sci. USA, Dec. 2012, 109(52):E3678-3686.

Brancucci et al., "Heterochromatin protein 1 secures survival and transmission of malaria parasites," Cell Host Microbe., Aug. 2014, 16(2):165-176.

De Koning-Ward et al., "Advances in molecular genetic systems in malaria," Nat. Rev. Microbiol., Jun. 2015, 13(6):373-387.

Ganesan et al., "Synthetic RNA-protein modules integrated with native translation mechanisms to control gene expression in malaria parasites," Nat. Commun., Mar. 2016, 7:10727, 10 pages.

International Preliminary Report on Patentability in International Appln. No. PCT/US2021/055201, mailed on May 4, 2023, 8 pages.

International Search Report and Written Opinion in International Appln. No. PCT/US2021/055201, mailed on Mar. 10, 2022, 12 pages.

Josling et al., "Regulation of Sexual Commitment and Gametocytogenesis in Malaria Parasites," Annu. Rev. Microbial., Sep. 2018, 72:501-519.

Kafsack et al., "A transcriptional switch underlies commitment to sexual development in malaria parasites," Nature, Mar. 2014, 507(7491):248-252.

Kent et al., "Inducible developmental reprogramming redefines commitment to sexual development in the malaria parasite *Plasmodium berghei*," Nat. Microbiol., Nov. 2018, 3(11):1206-1213.

Llora-Batlle et al., "Conditional expression of PfAP2-G for controlled massive sexual conversion in Plasmodium falciparum," Sci. Adv., Jun. 2020, 6(24):eaaz5057, 17 pages.

Lopez-Rubio et al., "Genome-wide analysis of heterochromatin associates clonally variant gene regulation with perinuclear repressive centers in malaria parasites," Cell Host Microbe., Feb. 2009, 5(2):179-190.

Muralidharan et al., "Asparagine repeat function in a Plasmodium falciparum protein assessed via a regulatable fluorescent affinity tag," Proc. Natl. Acad. Sci. USA, Mar. 2011, 108(11):4411-4416.

Poran et al., "Single-cell RNA sequencing reveals a signature of sexual commitment in malaria parasites," Nature, Nov. 2017, 551(7678):95-99.

Prommana et al., "Inducible Knockdown of Plasmodium Gene Expression Using the glmS Ribozyme," PLoS One, Aug. 2013, 8(8):e73783, 10 pages.

Sinha et al., "A cascade of DNA-binding proteins for sexual commitment and development in Plasmodium, " Nature, Mar. 2014, 507(7491):253-257.

* cited by examiner

*Primary Examiner* — Robert J Yamasaki
(74) *Attorney, Agent, or Firm* — Fish & Richardson P.C.

(57) ABSTRACT

This document relates to sexual stage *Plasmodium* parasites. For example, *Plasmodium* parasites having (e.g., engineered to have) a regulatable AP2-G polypeptide that can be induced to enter the sexual stage are provided.

20 Claims, 4 Drawing Sheets

Specification includes a Sequence Listing.

MATERIALS AND METHODS FOR MAKING SEXUAL STAGE PLASMODIUM PARASITES

CROSS-REFERENCE TO RELATED APPLICATIONS

This application is a National Stage application under 35 U.S.C. § 371 of International Application No. PCT/US2021/055201, having an International Filing Date of Oct. 15, 2021, which claims priority to, and the benefit of, U.S. Patent Application Ser. No. 63/094,280, filed on Oct. 20, 2020. The disclosure of each is considered part of (and is incorporated by reference in) the disclosure of this application.

STATEMENT REGARDING FEDERAL FUNDING

This invention was made with government support under Grant Nos. AI125565 and AI076276 awarded by the National Institutes of Health. The Government has certain rights in the invention.

SEQUENCE LISTING

This document contains a Sequence Listing that is being submitted electronically as an ASCII text file named 14017-0100WO1_Sequence_Listing.txt. The ASCII text file, created on Oct. 14, 2021, is 1,070 bytes in size. The material in the ASCII text file is hereby incorporated by reference in its entirety

TECHNICAL FIELD

This document relates to sexual stage *Plasmodium* parasites. For example, this document provides *Plasmodium* parasites having (e.g., engineered to have) nucleic acid encoding an apicomplexan 2 transcription factor G (AP2-G) polypeptide with the ability to be regulated in a manner that allows for *Plasmodium* parasites to be induced to enter the sexual stage. Also provided herein are methods and materials for making and using sexual stage *Plasmodium* parasites described herein.

BACKGROUND INFORMATION

Malaria is a major public health problem worldwide. It is a leading cause of death and disease in many developing countries, with young children and pregnant women being the most vulnerable (*World malaria report* 2017. Geneva: World Health Organization (2017)). In 2018, there were an estimated 228 million cases of malaria worldwide with an estimated 405,000 deaths (*World malaria report* 2017. Geneva: World Health Organization (2017)).

Malaria is caused by the replication of *Plasmodium* parasites (e.g., members of the *Plasmodium* genus) in human blood. *Plasmodium* parasites are spread to humans through the bites of infected female *Anopheles* mosquitoes. Current malaria vaccine development strategies rely on robust in vitro production of sexual stage *Plasmodium* parasites (gametocytes) for mosquito infection, and rely on genetically-, chemically-, or radiation-attenuated whole-cell sporozoites dissected from mosquito salivary glands. However, a major bottleneck for the production and deployment of such vaccines is the low conversion frequency from the asexual to sexual blood stage forms. In every 48-hour round of replication, a majority of *Plasmodium* parasites remain in a cycle of asexual blood stage replication, while only a small percentage of parasites (0-10%) commit to gametocytogenesis (e.g., exit asexual growth and convert to sexual stage *Plasmodium* parasites).

SUMMARY

The AP2-G transcription factor is a key regulator of sexual stage development in both *Plasmodium falciparum* and *P. berghei* (Kafsack et al., *Nature,* 507(7491):248-52 (2014); and Sinha et al., *Nature,* 507(7491):253-257 (2014)), and the ap2-g chromosomal locus of *Plasmodium* parasites is repressed at the epigenetic level through histone modifications of the ap2-g locus (Josling et al., *Annu Rev Microbiol.,* 72:501-519 (2018)). Cells that are positive for AP2-G can become gametocytes, but the ap2-g gene encoding the AP2-G polypeptide is epigenetically silenced in >90% of cells (Brancucci et al., *Cell Host Microbe.,* 16(2):165-176 (2014); and Lopez-Rubio et al., *Cell Host Microbe.,* 5(2):179-90 (2009)).

This document provides sexual stage *Plasmodium* parasites. For example, this document provides *Plasmodium* parasites having (e.g., engineered to have) regulatable AP2-G polypeptide expression. In some cases, *Plasmodium* parasites having (a) nucleic acid encoding a destabilization domain fused to the 3' end of nucleic acid (e.g., endogenous nucleic acid) encoding an AP2-G polypeptide and (b) one or more (e.g., one, two, three, four, five, six, seven, eight, nine, or more) disruptions in at least one pairing element flanking an ap2-g locus (e.g., an endogenous ap2-g locus) (e.g., one or more disruptions in the 5' pairing element and/or the 3' pairing element flanking endogenous nucleic acid encoding an AP2-G polypeptide fused to nucleic acid encoding a destabilization domain) can be induced to commit to gametocytogenesis (e.g., can be induced to exit asexual growth cycles and enter the sexual stage). Also provided herein are methods and materials for making and using sexual stage *Plasmodium* parasites described herein (e.g., *Plasmodium* parasites having regulatable AP2-G polypeptide expression).

As demonstrated herein, sexual stage *P. falciparum* can be generated by engineering *P. falciparum* to express a regulatable AP2-G polypeptide and to have a reduced level of epigenetic silencing of the *P. falciparum* ap2-g (pfap2-g) locus. A regulatable AP2-G polypeptide can be generated by fusing a destabilization domain derived from a FK506-binding protein (FKBP) polypeptide to an AP2-G polypeptide such that in the absence of a Shield-1 (Shld1) molecule, the FKBP destabilization domain is unstable and the fusion polypeptide is targeted for proteolytic degradation. And, in the presence of a Shld1 molecule, the FKBP destabilization domain is stabilized and expression of the fusion polypeptide is maintained. The level of epigenetic silencing of the pfap2-g locus can be reduced or eliminated by disruption of at least one of the cis regulatory pairing elements flanking the pfap2-g locus. Also as demonstrated herein, in the present of a Shld1 molecule, over 60% of *P. falciparum* expressing a regulatable AP2-G polypeptide and having a reduced level of histone modification at the 3' pairing element of the pfap2-g locus can commit to gametocytogenesis and form sexual stage parasites.

Having the ability to regulate AP2-G polypeptide expression and to reduce or eliminate epigenetic silencing of the endogenous ap2-g locus in *Plasmodium* parasites as described herein provides a unique and unrealized opportunity to effectively and efficiently generate sexual stage *Plasmodium* parasites. For example, the engineered *Plas-*

*modium* parasites provided herein can allow sexual stage parasites to be obtained in bulk, in vitro, in any laboratory.

In general, one aspect of this document features *Plasmodium* parasites. The genome of the *Plasmodium* parasite can include: (a) exogenous nucleic acid encoding a destabilization domain fused to the 3' end of nucleic acid encoding an AP2-G polypeptide, and (b) at least one disrupted pairing element, where the disrupted pairing element includes a disruption in a pairing element flanking the nucleic acid encoding the AP2-G polypeptide fused to the nucleic acid encoding the destabilization domain. The *Plasmodium* can be a *P. falciparum*, a *P. berghei*, a *P. voelii*, a *P. vivax*, a *P. malariae*, a *P. ovale*, or a *P. knowlesi*. For example, the *Plasmodium* parasite can be a *P. falciparum*. The destabilization domain can include a FKBP destabilization domain. The destabilization domain can include a glmS ribozyme. The exogenous nucleic acid encoding a destabilization domain can include nucleic acid encoding a peptide tag. The peptide tag can be an HA tag, a Myc-tag, a FLAG-tag, or a T7-tag. The disrupted pairing element can include a disruption as compared to a pairing element set forth in SEQ ID NO:1, SEQ ID NO:2, or SEQ ID NO:3. The disrupted pairing element can include a sequence as set forth in SEQ ID NO:4. The disrupted pairing element can be a 5' pairing element. The disrupted pairing element can be a 3' pairing element. The genome of the *Plasmodium* parasite can include a disrupted 5' pairing element and a disrupted 3' pairing element.

In another aspect, this document features methods for generating sexual stage *Plasmodium* parasites. The methods can include, or consist essentially of, administering a ligand to a *Plasmodium* parasite having a regulatable AP2-G polypeptide, where the genome of the *Plasmodium* parasite includes: (a) exogenous nucleic acid encoding a destabilization domain fused to the 3' end of nucleic acid encoding an AP2-G polypeptide, and (b) at least one disrupted pairing element, where the disrupted pairing element includes a disruption in a pairing element flanking the nucleic acid encoding the AP2-G polypeptide fused to the nucleic acid encoding the destabilization domain; where the ligand stabilizes the destabilization domain, and where the stabilization is effective to increase the level of AP2-G polypeptide present within the *Plasmodium* parasite. The *Plasmodium* parasite can be a *P. falciparum*, a *P. berghei*, a *P. voelii*, a *P. vivax*, a *P. malariae*, a *P. ovale*, or a *P. knowlesi*. For example, the *Plasmodium* parasite can be a *P. falciparum*. The destabilization domain can include a FKBP destabilization domain. The ligand can be a Shld1 molecule. The destabilization domain can include a glmS ribozyme. The ligand can be N-acetyl glucosamine. The exogenous nucleic acid encoding a destabilization domain can include nucleic acid encoding a peptide tag. The peptide tag can be an HA tag, a Myc-tag, a FLAG-tag, or a T7-tag. The disrupted pairing element can include a disruption as compared to a pairing element set forth in SEQ ID NO:1, SEQ ID NO:2, or SEQ ID NO:3. The disrupted pairing element can include a sequence as set forth in SEQ ID NO:4. The disrupted pairing element can be a 5' pairing element. The disrupted pairing element can be a 3' pairing element. The genome of the *Plasmodium* parasite can include a disrupted 5' pairing element and a disrupted 3' pairing element.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
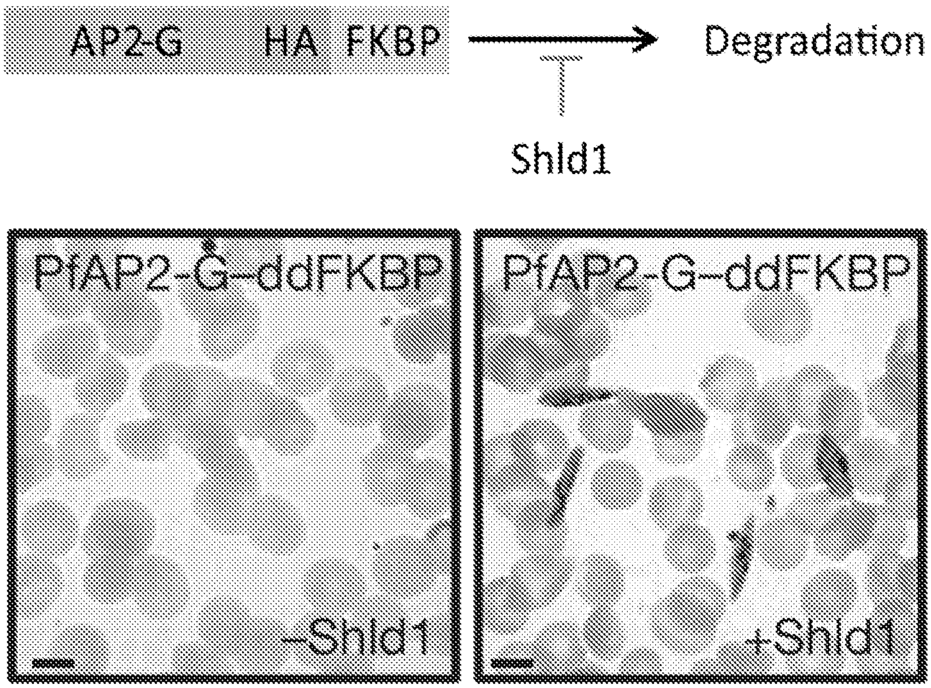
FIG. 1: Conditional knockdown of a PfAP2-G polypeptide. The FKBP destabilization domain can be used to conditionally deplete PfAP2-G polypeptides in the absence of Shield 1 (Shld1), while the presence of Shld1 stabilizes the FKBP-tagged PfAP2-G polypeptide leading to gametocyte production.

This document provides methods and materials for producing sexual stage *Plasmodium* parasites efficiently and effectively. For example, this document provides *Plasmodium* parasites having (e.g., engineered to have) regulatable AP2-G polypeptide expression. For example, this document provides *Plasmodium* parasites having (e.g., engineered to have) nucleic acid encoding a destabilization domain fused to the 3' end of nucleic acid (e.g., endogenous nucleic acid) encoding an AP2-G polypeptide and having one or more (e.g., one, two, three, four, five, six, seven, eight, nine, or more) disruptions in at least one pairing element flanking the ap2-g locus (e.g., one or more disruptions in the 5' pairing element and/or the 3' pairing element flanking endogenous nucleic acid encoding an AP2-G polypeptide fused to nucleic acid encoding a destabilization domain). Such *Plasmodium* parasites can be induced to enter the sexual stage. Also provided herein are methods and materials for making and using sexual stage *Plasmodium* parasites described herein (e.g., *Plasmodium* parasites having regulatable AP2-G polypeptide expression and induced to enter the sexual stage). As described herein, *Plasmodium* parasites having nucleic acid encoding a destabilization domain fused to the 3' end of nucleic acid (e.g., endogenous nucleic acid) encoding an AP2-G polypeptide, and having one or more disruptions in at least one pairing element flanking the endogenous ap2-g locus (e.g., one or more disruptions in the 5' pairing element and/or the 3' pairing element flanking endogenous nucleic acid encoding an AP2-G polypeptide fused to nucleic acid encoding a destabilization domain) can be induced (e.g., in the presence of a ligand that can stabilize the destabilization domain) to commit to gametocytogenesis (e.g., can be induced to exit asexual growth cycles and enter the sexual stage).

*Plasmodium* parasites described herein (e.g., *Plasmodium* parasites having regulatable AP2-G polypeptide expression)

can be any species of *Plasmodium* parasite (e.g., any *Plasmodium* spp.). Examples of *Plasmodium* spp. include, without limitation, *P. falciparum*, *P. berghei*, *P. voelii*, *P. vivax*, *P. malariae*, *P. ovale*, and *P. knowlesi*.

In some cases, *Plasmodium* parasites described herein (e.g., *Plasmodium* parasites having regulatable AP2-G polypeptide expression) can use a destabilization domain to regulate AP2-G expression. For example, *Plasmodium* parasites can have (e.g., can be engineered to have) nucleic acid encoding a destabilization domain fused to the 3' end of nucleic acid (e.g., endogenous nucleic acid) encoding an AP2-G polypeptide. A nucleic acid encoding a destabilization domain fused to the 3' end of nucleic acid (e.g., the endogenous nucleic acid) encoding an AP2-G polypeptide can be exogenous nucleic acid. A nucleic acid encoding a destabilization domain fused to the 3' end of nucleic acid (e.g., endogenous nucleic acid) encoding an AP2-G polypeptide can be a recombinant nucleic acid. The term "destabilizing domain" as used herein refers to both polypeptide-based destabilizing domains and RNA-based destabilizing domains. In some cases, AP2-G polypeptide-encoding nucleic acid having nucleic acid encoding a destabilization domain fused to its 3' end can encode an AP2-G polypeptide fused to a polypeptide-based destabilization domain (an AP2G-DD polypeptide). In some cases, AP2-G polypeptide-encoding nucleic acid having nucleic acid encoding a destabilization domain fused to its 3' end can produce an RNA molecule (e.g., a messenger RNA (mRNA)) including an AP2-G transcript fused to an RNA-based destabilization domain. Examples of polypeptide-based destabilization domains that can be used as described herein include, without limitation, a FKBP destabilization domain (e.g., a destabilization domain derived from a FKBP polypeptide), and a dihydrofolate reductase (DHFR) destabilization domain (e.g., a destabilization domain derived from a DHFR polypeptide). Examples of RNA-based destabilization domains that can be used as described herein include, without limitation, a glucosamine-6-phosphate riboswitch ribozyme (glmS ribozyme), and TetR-DOZI/aptamer module. In some cases, a destabilization domain can be as described in Example 1 or Example 4. In some cases, a destabilization domain can be as described elsewhere (see, e.g., de Koning-Ward et al., *Nature Reviews|Microbiology,* 13:373-387 (2015); Prommana et al., *PLoS One,* 8(8): e73783 (2013); Muralidharan et al., *PNAS,* 108(11):4411-4416 (2011); and Ganesan et al., *Nat. Commun.,* 7:10727 (2016)).

A destabilization domain can be stabilized by a ligand (e.g., an exogenous ligand). For example, in the presence of a ligand that can target (e.g., target and bind to) the destabilization domain, an AP2G-DD polypeptide or a mRNA including an AP2-G transcript fused to an RNA-based destabilization domain can be stabilized, and gametocytes can be produced (e.g., the *Plasmodium* parasites commit to gametocytogenesis). However, in the absence of a ligand that can target (e.g., target and bind to) and stabilize the destabilization domain, an AP2G-DD polypeptide or a mRNA including an AP2-G transcript fused to an RNA-based destabilization domain can be unstable and degraded (e.g., targeted for proteolytic degradation), and gametocytes are not produced (e.g., the *Plasmodium* parasites do not commit to gametocytogenesis). When nucleic acid encoding an AP2-G polypeptide has nucleic acid encoding a destabilization domain fused to its 3' end and encodes an AP2G-DD polypeptide, the AP2G-DD polypeptide can be stable in the presence of a ligand that can target (e.g., target and bind to) the destabilization domain, and can be degraded in the absence of the ligand. When nucleic acid encoding an AP2-G polypeptide has nucleic acid encoding a destabilization domain fused to its 3' end and produces a mRNA including an AP2-G transcript fused to an RNA-based destabilization domain, the AP2-G transcript fused to the RNA-based destabilization domain can be stable in the presence of a ligand that can target (e.g., target and bind to) the destabilization domain (e.g., such that an AP2-G polypeptide is encoded by the mRNA), and that transcript can be degraded in the absence of the ligand.

A ligand that can stabilize a destabilization domain described herein can be any appropriate ligand. Examples of destabilization domain ligands that can be used as described herein include, without limitation, (a) a Shld1 molecule when using a FKBP destabilization domain, (b) N-acetyl glucosamine when using a glmS ribozyme destabilization domain, (c) trimethoprim when using a DHFR destabilization domain; and (d) anhydrous tetracycline when using a TetR-DOZI/aptamer module. For example, when a polypeptide-based destabilization domain is a FKBP destabilization domain, the destabilization domain (e.g., a destabilization domain on an AP2G-DD polypeptide) can be stabilized by a Shld1 molecule. For example, when an RNA-based destabilization domain is a glmS ribozyme, the glmS ribozyme (e.g., a glmS ribozyme on an AP2-G transcript) can be stabilized (e.g., stabilized and activated) by N-acetyl glucosamine.

In some cases, nucleic acid encoding a tag can be fused to nucleic acid (e.g., endogenous nucleic acid) encoding an AP2-G polypeptide (e.g., can be fused to the 3' end of endogenous nucleic acid encoding an AP2-G polypeptide). Nucleic acid encoding a tag can be exogenous nucleic acid. Nucleic acid encoding a tag can be recombinant nucleic acid. A tag can be any appropriate tag. In some cases, a tag can be a peptide tag. Examples of tags that can be fused to nucleic acid (e.g., endogenous nucleic acid) encoding an AP2-G polypeptide or included with nucleic acid encoding a destabilization domain that is fused to the 3' end of nucleic acid (e.g., endogenous nucleic acid) encoding an AP2-G polypeptide described herein include, without limitation, an HA tag, a Myc-tag, a FLAG-tag a T7-tag, a FKBP destabilization domain, and a DHFR destabilization domain.

In some cases, *Plasmodium* parasites described herein (e.g., *Plasmodium* parasites having regulatable AP2-G polypeptide expression) can be designed such that an inducible expression system can be used to regulate AP2-G expression. Examples of inducible expression systems that can be used to regulate AP2-G expression in *Plasmodium* parasites as described herein include, without limitation, a Cre/Lox recombinase system (e.g., a CreER system that can be induced by tamoxifen), and a tetracycline (Tet) system (e.g., a Tet-On system that can be induced by tetracycline or a tetracycline derivative such as doxycycline). When a Cre/Lox recombinase system is used to regulate AP2-G expression in *Plasmodium* parasites, the Cre/Lox recombinase system can be designed to operably link nucleic acid encoding an AP2-G polypeptide to a promoter. The term "operably linked" as used herein refers to positioning a regulatory element (e.g., a promoter sequence) relative to a nucleic acid sequence encoding a polypeptide to permit or facilitate expression of the encoded polypeptide. In the nucleic acid described herein, for example, a Cre/Lox recombinase system can be used to position a promoter sequence 5' of nucleic acid encoding an AP2-G polypeptide (e.g., the endogenous ap2-g gene) such that the promoter sequence can facilitate expression of the encoded polypeptide. A promoter sequence can be a naturally occurring promoter sequence or a recombinant promoter sequence. In some cases, a promoter sequence can be a synthetic promoter sequence. In some cases, a promoter sequence can be a constitutively active promoter sequence. In some cases, a promoter sequence can be a regulated (e.g., an inducible) promoter sequence. Examples of promoter sequences that can be operably linked to a nucleic acid sequence encoding an AP2-G polypeptide include, without limitation, a calmodulin promoter, a hsp70 promoter, a hsp86 promoter, a hrp3 promoter, and an endogenous ap2-g promoter. For example, a Cre/Lox recombinase system can be used to operably link a nucleic acid sequence encoding an AP2-G polypeptide to a calmodulin promoter to regulate AP2-G expression. For example, a *Plasmodium* parasites can have (e.g., can be engineered to have) a nucleic acid including an inverted promoter (e.g., a constitutive promoter such as a calmodulin promoter) that is flanked by loxP sites located 5' to the endogenous ap2-g locus such that the nucleic acid including a promoter flanked by loxP sites can uncouple the endogenous ap2-g gene from its native promoter, and where the presence of one or more Cre recombinase polypeptides can invert the promoter such that the promoter can drive expression of the endogenous ap2-g gene. In some cases, a Cre/Lox recombinase system can be used to regulate AP2-G expression as described elsewhere (see, e.g., Kent et al., *Nat Microbiol.,* 3(11):1206-1213 (2018); and Llorà-Batlle et al., Sci. Adv., 6(24):eaaz5057 (2020)).

*Plasmodium* parasites described herein (e.g., *Plasmodium* parasites having regulatable AP2-G polypeptide expression) can have (e.g., can be engineered to have) one or more disruptions in at least one pairing element flanking the endogenous ap2-g locus (e.g., one or more disruptions in the 5' pairing element and/or the 3' pairing element flanking endogenous nucleic acid encoding an AP2-G polypeptide fused to nucleic acid encoding a destabilization domain). The term "reduced level" as used herein with respect to a level of epigenetic silencing of the ap2-g locus refers to any level that is lower than a reference level of epigenetic silencing of the ap2-g locus. The term "reference level" as used herein with respect to epigenetic silencing of the ap2-g locus refers to the level of epigenetic silencing of the ap2-g locus typically observed in *Plasmodium* parasites not genetically modified as described herein. In some cases, a reduced level of epigenetic silencing of the ap2-g locus can be an undetectable level of epigenetic silencing. In some cases, a reduced level of epigenetic silencing of the ap2-g locus can be a level where epigenetic silencing of the ap2-g locus is eliminated. For example, *Plasmodium* parasites having a reduced level of epigenetic silencing of the ap2-g locus can have at least 50 percent (e.g., at least 60 percent, at least 75 percent, at least 90 percent, or at least 97 percent) less epigenetic silencing of the ap2-g locus as compared to control *Plasmodium* parasites (e.g., *Plasmodium* parasites not genetically modified as described herein such as wild-type *Plasmodium* parasites). For example, *Plasmodium* parasites having a reduced level of epigenetic silencing of the ap2-g locus can have epigenetic silencing of the ap2-g locus in less than about 90 percent (e.g., less than about 80 percent, less than about 70 percent, less than about 60 percent, less than about 50 percent, less than about 40 percent, less than about 30 percent, less than about 25 percent, 25 less than about 20 percent, less than about 15 percent, less than about 10 percent, less than about 7 percent, less than about 5 percent, less than about 2 percent, or less than about 1 percent) of the cells within the *Plasmodium* parasites.

A level of epigenetic silencing of the ap2-g locus can be measured using any appropriate technique. In some cases, a level of epigenetic silencing of the ap2-g locus can be measured using chromatin immunoprecipitation (e.g., chromatin immunoprecipitation of H3K9me3 histones), and/or next-generation sequencing (ChIP-seq) techniques. In some cases, a level of epigenetic silencing of the ap2-g locus can be measured as described in Example 2.

*Plasmodium* parasites described herein (e.g., *Plasmodium* parasites having regulatable AP2-G polypeptide expression) can have (e.g., can be engineered to have) one or more (e.g., one, two, three, four, five, six, seven, eight, nine, or more) disruptions in at least one pairing element flanking the ap2-g locus (e.g., one or more disruptions in the 5' pairing element and/or the 3' pairing element flanking endogenous nucleic acid encoding an AP2-G polypeptide fused to nucleic acid encoding a destabilization domain). In some cases, a pairing element can be an insulator-like pairing element. In some cases, *Plasmodium* parasites described herein can have one or more disruptions in 5' pairing element flanking the endogenous ap2-g locus. In some cases, *Plasmodium* parasites described herein can have one or more disruptions in the 3' pairing element flanking the endogenous ap2-g locus. In some cases, *Plasmodium* parasites described herein can have one or more disruptions in the 5' pairing element flanking the endogenous ap2-g locus and can have one or more disruptions in the 3' pairing element flanking the endogenous ap2-g locus.

*Plasmodium* parasites described herein (e.g., *Plasmodium* parasites having regulatable AP2-G polypeptide expression) can have (e.g., can be engineered to have) any appropriate disruption(s) in at least one pairing element flanking the ap2-g locus (e.g., one or more disruptions in the 5' pairing element and/or the 3' pairing element flanking endogenous nucleic acid encoding an AP2-G polypeptide fused to nucleic acid encoding a destabilization domain). In some cases, one or more disruptions in at least one pairing element flanking the ap2-g locus can be effective to reduce or eliminate epigenetic silencing of the ap2-g locus. For example, one or more disruptions in a pairing element flanking the endogenous ap2-g locus can reduce or eliminate methylation of one or more histones at the pairing element. For example, one or more disruptions in a pairing element flanking the endogenous ap2-g locus can increase acetylation of one or more histones at the pairing element. For example, one or more disruptions in a pairing element flanking the endogenous ap2-g locus can reduce or eliminate binding of one or more repressive histones at the pairing element. A pairing element flanking the ap2-g locus and having one or more disruptions can be referred to as a disrupted pairing element.

Figure 2:
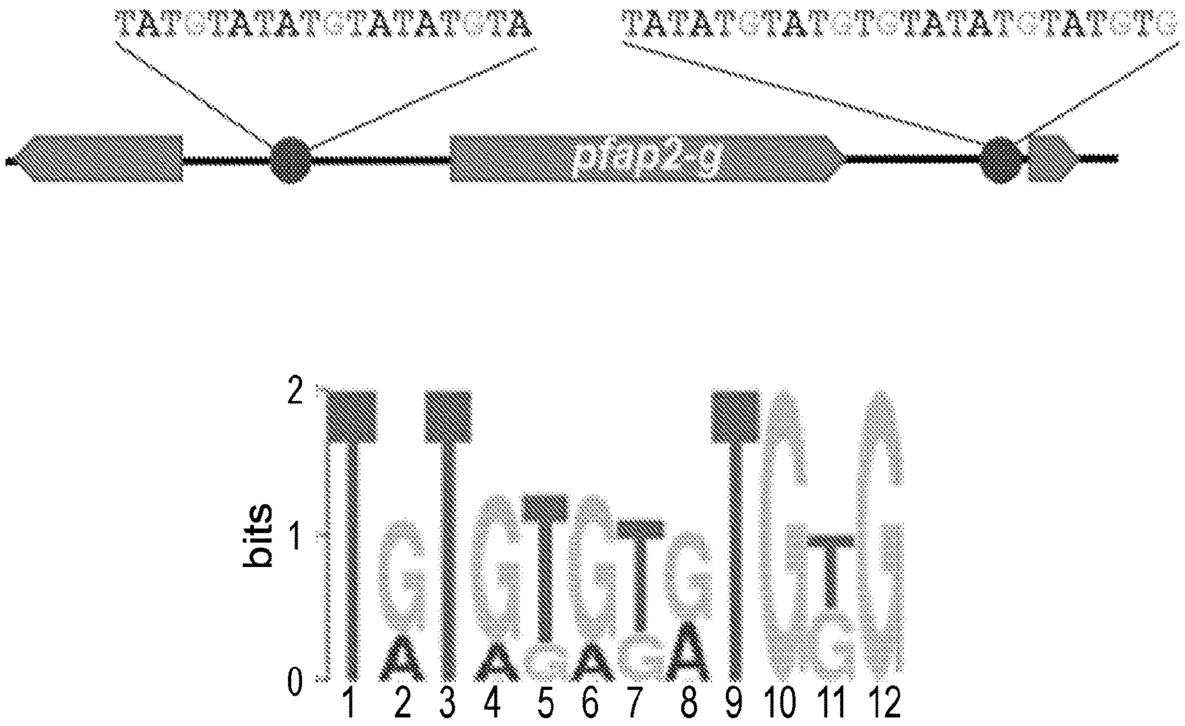
FIG. 2: The locations and sequences of an exemplary 5' pairing element (SEQ ID NO:1) and an exemplary 3' pairing element (SEQ ID NO:2) flanking the pfap2-g locus. Also shown is a motif of the pairing element (SEQ ID NO:3).

The term "disruption" as used herein with reference to at least one pairing element flanking the endogenous ap2-g locus (e.g., one or more disruptions in the 5' pairing element and/or the 3' pairing element flanking endogenous nucleic acid encoding an AP2-G polypeptide fused to nucleic acid encoding a destabilization domain) refers to any genetic modification (e.g., nucleotide deletions, additions, insertions and deletions (indels), inversions, and/or substitutions) of at least one pairing element flanking the endogenous ap2-g locus as compared to control pairing elements flanking the ap2-g locus (e.g., *Plasmodium* parasites not genetically modified as described herein such as wild-type *Plasmodium* parasites). In some cases, a disruption can be a substitution of one or more nucleotides within a pairing element as compared to control pairing elements flanking the ap2-g locus. For example, a disruption can be a substitution as compared to a pairing element flanking the ap2-g locus as shown in FIG. 2. For example, a disruption can be a substitution as compared to a pairing element flanking the ap2-g locus that has a nucleic acid sequence set forth in SEQ ID NO:1, a nucleic acid sequence set forth in SEQ ID NO:2, or a nucleic acid sequence set forth in SEQ ID NO:3. In some cases, a disruption can be a deletion of one or more nucleotides within a pairing element as compared to control pairing elements flanking the ap2-g locus. For example, a disruption can be a deletion of at least one pairing element (e.g., the 5' pairing element and/or the 3' pairing element) as compared to a pairing element flanking the ap2-g locus. In some cases, a disruption can be effective to reduce or eliminate a level of histone modification at the disrupted pairing element.

A disrupted pairing element described herein (e.g., a pairing element flanking endogenous nucleic acid encoding an AP2-G polypeptide fused to nucleic acid encoding a destabilization domain and having one or more disruptions) can be any appropriate length (e.g., can include any appropriate number of nucleotides). For example, a disrupted pairing element can include from about 0 to about 25 (e.g., from about 0 to about 25, from about 0 to about 22, from about 0 to about 20, from about 0 to about 18, from about 0 to about 15, from about 0 to about 12, from about 0 to about 10, from about 0 to about 7, from about 0 to about 5, from about 5 to about 25, from about 10 to about 25, from about 15 to about 25, from about 20 to about 25, from about 5 to about 20, from about 10 to about 15, from about 5 to about 15, or from about 10 to about 20) nucleotides. In some cases, a disrupted pairing element can include about 18 nucleotides (e.g., a disrupted 5' pairing element can include about 18 nucleotides). In some cases, a disrupted pairing element can include about 24 nucleotides (e.g., a disrupted 3' pairing element can include about 24 nucleotides).

A disrupted pairing element described herein (e.g., a pairing element flanking endogenous nucleic acid encoding an AP2-G polypeptide fused to nucleic acid encoding a destabilization domain and having one or more disruptions) can include any number of disruptions. For example, a disrupted pairing element can include from about 1 to about 10 (e.g., from about 1 to about 8, from about 1 to about 6, from about 1 to about 4, from about 3 to about 10, from about 5 to about 10, from about 7 to about 10, from about 2 to about 8, from about 4 to about 6, from about 2 to about 5, or from about 5 to about 8) disruptions. In some cases, a disrupted pairing element can include about 8 disruptions. For example, when an undisrupted 5' pairing element includes about 18 nucleotides, the disrupted 5' pairing element can include 8 substitutions. In some cases, a disrupted pairing element can include about 6 disruptions. For example, when an undisrupted 3' pairing element includes about 24 nucleotides, the disrupted 3' pairing element can include 6 substitutions.

Figure 3:
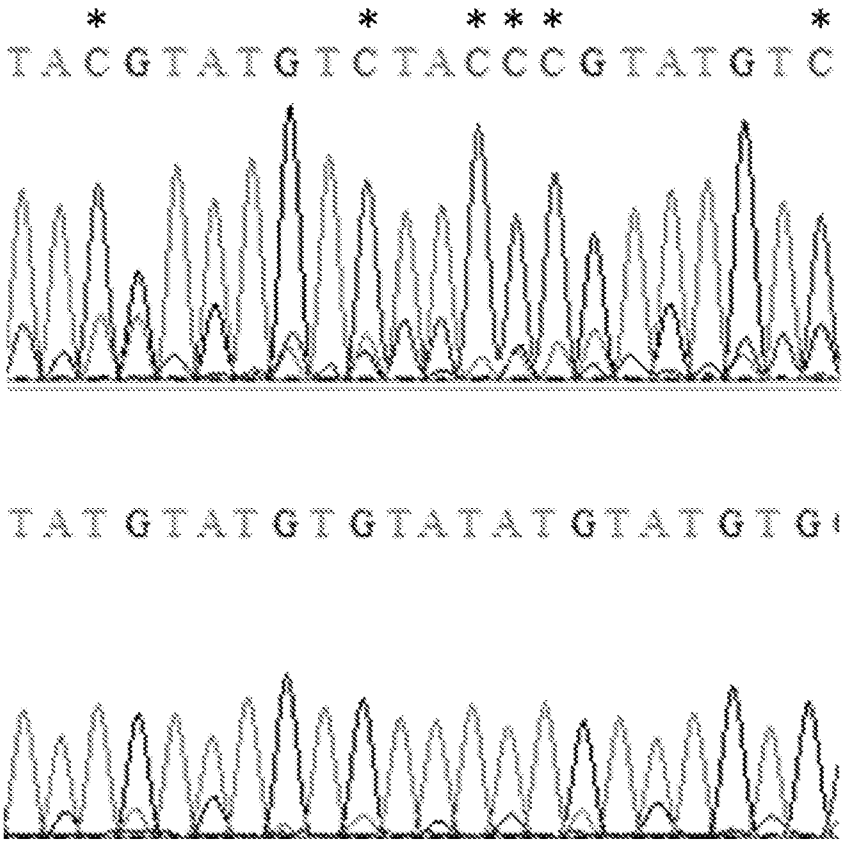
FIG. 3: An exemplary mutation of the 3' pfap2-g pairing element (SEQ ID NO:4) by CRISPR/Cas9 (top). Bottom is the wild type sequence (SEQ ID NO:5).

A disrupted pairing element described herein (e.g., a pairing element flanking endogenous nucleic acid encoding an AP2-G polypeptide fused to nucleic acid encoding a destabilization domain and having one or more disruptions) can have any appropriate nucleic sequence. For example, a disrupted pairing element can be as shown in FIG. 3. For example, a disrupted pairing element can have a nucleic acid sequence that includes the nucleic acid sequence set forth in SEQ ID NO:4.

Any suitable method can be used to generate *Plasmodium* parasites described herein (e.g., *Plasmodium* parasites having regulatable AP2-G polypeptide expression). For example, molecular cloning technologies, gene editing technologies (e.g., CRISPR/Cas9, TALENS, and Zinc-finger technologies), site-specific recombinase technologies, and homologous recombination technologies can be used to fuse nucleic acid encoding a destabilization domain to the 3' end of the endogenous nucleic acid encoding an AP2-G polypeptide. In some cases, nucleic acid encoding a destabilization domain can be fused to the 3' end of the endogenous nucleic acid encoding an AP2-G polypeptide as described in Example 1. In some cases, nucleic acid encoding a destabilization domain can be fused to the 3' end of the endogenous nucleic acid encoding an AP2-G polypeptide as described elsewhere (see, e.g., de Koning-Ward et al., *Nature Reviews|Microbiology,* 13:373-387 (2015); and Prommana et al., *PLoS One,* 8(8):e73783 (2013)). For example, gene editing technologies (e.g., CRISPR/Cas9, TALENS, and Zinc-finger technologies), site-specific recombinase technologies, and homologous recombination technologies can be used to generate one or more disruptions in at least one pairing element flanking the endogenous ap2-g locus (e.g., one or more disruptions in the 5' pairing element and/or the 3' pairing element flanking endogenous nucleic acid encoding an AP2-G polypeptide fused to nucleic acid encoding a destabilization domain). In some cases, one or more disruptions in at least one pairing element flanking the endogenous ap2-g locus can be generated as described in Example 2. In some cases, one or more disruptions in at least one pairing element flanking the endogenous ap2-g locus can be generated as described elsewhere (see, e.g., Avraham et al., *Proc Natl Acad Sci USA,* 109(52): E3678-86 (2012)).

In some cases, *Plasmodium* parasites described herein (e.g., *Plasmodium* parasites having regulatable AP2-G polypeptide expression) lack modified expression levels of other endogenous polypeptides (e.g., endogenous *Plasmodium* polypeptides other than an AP2-G polypeptide).

This document also provides methods and materials for using *Plasmodium* parasites described herein (e.g., *Plasmodium* parasites having regulatable AP2-G polypeptide expression). In some cases, *Plasmodium* parasites described herein can be used to produce gametocytes. For example, *Plasmodium* parasites described herein can be induced to commit to gametocytogenesis thereby producing gametocytes. When *Plasmodium* parasites described herein include nucleic acid encoding an FKBP destabilization domain fused to the 3' end of the endogenous nucleic acid encoding an AP2-G polypeptide and express an AP2-G polypeptide fused to an FKBP destabilization domain, the *Plasmodium* parasites can be induced to commit to gametocytogenesis in the presence of one or more Shld1 molecules. When *Plasmodium* parasites described herein include a nucleic acid encoding glmS ribozyme fused to the 3' end of the endogenous nucleic acid encoding an AP2-G polypeptide and express an AP2-G transcript fused to a glmS ribozyme destabilization domain, the *Plasmodium* parasites can be induced to commit to gametocytogenesis in the absence of N-acetyl glucosamine. *Plasmodium* parasites described herein can be induced to commit to gametocytogenesis with at least 50 percent (e.g., at least 60 percent, at least 75 percent, at least 90 percent, at least 95 percent, at least 97 percent, at least 98 percent, or at least 99 percent) efficiency. In some cases, *Plasmodium* parasites described herein can commit to gametocytogenesis with 100% efficiency.

In some cases, *Plasmodium* parasites described herein (e.g., *Plasmodium* parasites having regulatable AP2-G polypeptide expression) can be used to increase the number of mosquitos that can be infected by *Plasmodium* parasites (e.g., upon blood feeding). For example, mosquitos that are infected by *Plasmodium* parasites described herein can produce an increased number of oocysts produced per mosquito (e.g., as compared to a mosquito infected by control *Plasmodium* parasites such as *Plasmodium* parasites not genetically modified as described herein including, for example, wild-type *Plasmodium* parasites), thereby leading to an increased number of sporozoites.

In some cases, *Plasmodium* parasites described herein (e.g., *Plasmodium* parasites having regulatable AP2-G polypeptide expression) can be used to identify one or more molecules (e.g., one or more polypeptides or candidate small molecule drugs) that can be administered to a mammal for the prevention, amelioration, or treatment of malaria. For example, *Plasmodium* parasites described herein can be used to identify one or more immunogenic molecules that can be administered to a mammal in need thereof (e.g., a mammal having or at risk of developing malaria) to induce an immune response (e.g., an anti-malaria immune response) within the mammal. An anti-malaria immune response can be a protective immune response and/or a therapeutic immune response. In some cases, sporozoites produced by a mosquito as described herein (e.g., following infection of a mosquito with *Plasmodium* parasites described herein) can be isolated from the mosquito salivary glands and can be used to identify one or more molecules (e.g., immunogenic molecules) produced by *Plasmodium* sporozoites.

In some cases, *Plasmodium* parasites described herein (e.g., *Plasmodium* parasites having regulatable AP2-G polypeptide expression) can be used to identify, evaluate, and/or validate a therapeutic intervention for malaria. For example, *Plasmodium* parasites described herein can be used to identify one or more molecules that can be administered to a mammal in need thereof (e.g., a mammal having or at risk of developing malaria) to reduce or eliminate the number of *Plasmodium* parasites present within the mammal (e.g., can kill one or more *Plasmodium* parasites present within the mammal). In some cases, sporozoites produced by a mosquito as described herein (e.g., following infection of a mosquito with *Plasmodium* parasites described herein) can be isolated from the mosquito salivary glands and can be used to identify one or more molecules that can kill *Plasmodium* parasites.

In some cases, *Plasmodium* parasites described herein (e.g., *Plasmodium* parasites having regulatable AP2-G polypeptide expression) can be induced to commit to gametocytogenesis (e.g., can be induced to exit asexual growth cycles and enter the sexual stage), and the sexual stage *Plasmodium* parasites can be used to identify one or more molecules that can kill *Plasmodium* parasites. For example, a candidate therapeutic intervention (e.g., a test molecule) can be administered to *Plasmodium* parasites as described herein, and the *Plasmodium* parasites can be monitored for survival. Examples of test molecules that can be assessed for the ability to kill *Plasmodium* parasites as described herein include, without limitation, polypeptides, nucleic acid molecules encoding a polypeptide, and small molecules. In some cases, the members of a library of different test molecules (e.g., a library of different small molecules) can be assessed to identify individual members having the ability to kill *Plasmodium* parasites as described herein.

The invention will be further described in the following examples, which do not limit the scope of the invention described in the claims.

EXAMPLES

Example 1: Regulatable PfAP2-G Polypeptides

A regulatable knockdown of PfAP2-G was generated by engineering a transgenic line with AP2-G fused to an FKBP destabilization domain (DD) as described elsewhere (see, e.g., Kafsack et al., *Nature,* 507(7491):248-52 (2014)). Briefly, a construct encoding an AP2-G polypeptide fused to an HA-tag and an FKBP DD (e.g., an AP2-G-HA-FKBP polypeptide) was stably integrated into the genome of *Plasmodium falciparum* lines.

In the absence of the ligand Shield-1 (Shld1), the FKBP destabilization domain was unstable and targets fusion proteins for proteolytic degradation. However, in the presence of Shld1, the FKBP destabilization domain was stabilized, AP2-G-HA-FKBP expression was maintained, and gametocytes were produced (FIG. 1).

Example 2: Enhanced Production of Gametocytes by Modification of Pairing Elements Surrounding the ap2-g Gene The pfap2-g locus is flanked by short TG-rich sequences cis regulatory elements known as pairing elements or boundary elements that are required for epigenetic silencing the pfap2-g locus.

To determine whether mutation of the pairing elements can de-repress the pfap2-g locus and increase rates of sexual conversion, the pairing element sequences were mutated in AP2-G-HA-FKBP parasites grown in the absence of Shld1. The pairing element sequences flanking the pfap2-g locus and the consensus motif are shown in FIG. 2.

Figure 4:
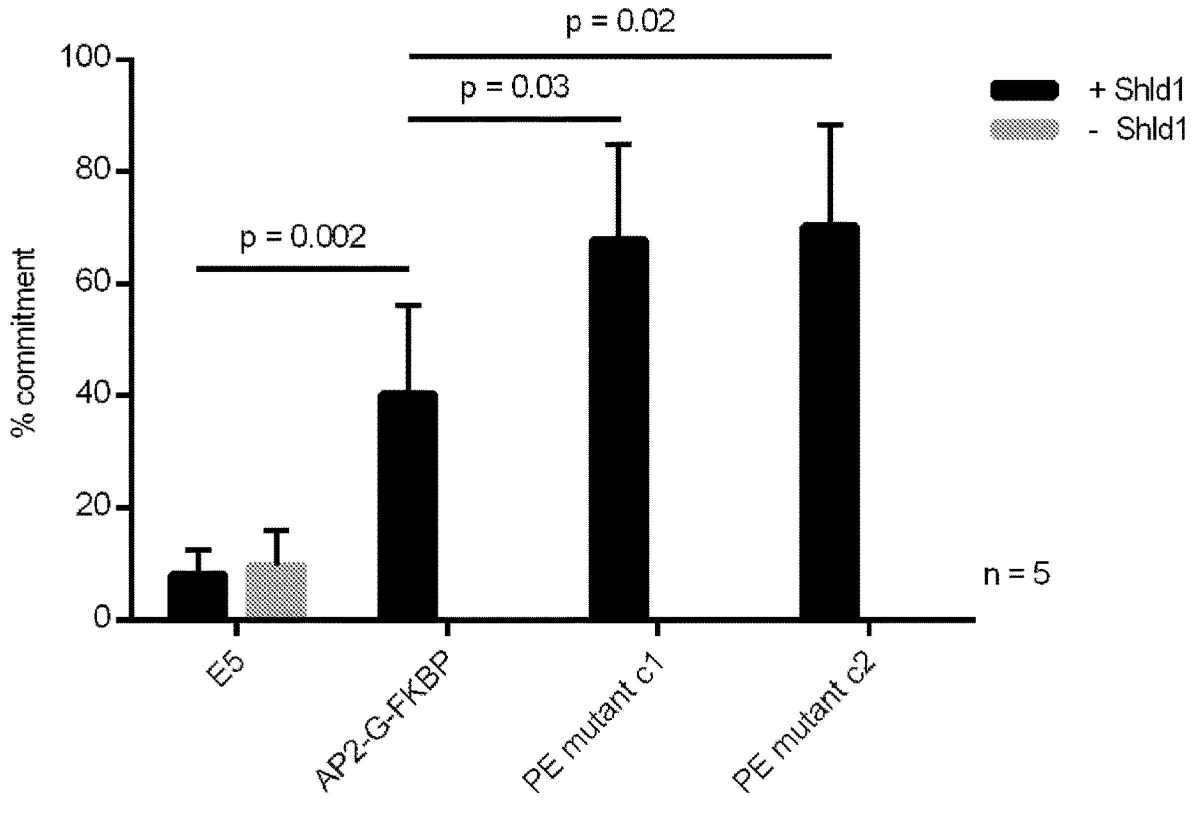
FIG. 4: Mutation of the 3' pfap2-g pairing element results in a significant increase in gametocyte commitment.

The mutated downstream 3' pairing element is shown in FIG. 3. In a triplicate assay performed in two different parasite clones having a mutated 3' pairing element, the deletion of the 3' pairing element resulted in a doubling of the number of gametocytes (FIG. 4).

Gene Editing

Gene editing is performed by designing sgRNAs to target either the 5' or 3' pairing element for targeted cleavage by the Cas9 protein. A homologous DNA template that flanks the cleavage site and contains the desired mutations to the pairing element is used for homologous recombination to repair the damaged DNA (~500-1000 base pairs in length). Recovered modified *Plasmodium* parasite lines are cloned by limiting dilution cloning and assessed for whether they contain the desired modification by genotyping PCR. Successful colonies are whole genome sequenced. Once validated, the level of histone binding is assessed using chromatin immunoprecipitation coupled with net generation sequencing (ChiP-seq) using antibodies against histone H3 as well as histone variants H3K9me3 and H3K9ace and using input DNA as a control for the immunoprecipitations.

Gametocytogenesis

The number of gametocytes was determined by splitting the culture in two and treating half with Shld1 and half with the same volume of the vehicle (Day 1). The parental cell line (AP2-G-HA-FKBP) and the pairing element mutant were tested in parallel. After 48 hours (on Day 3), the number of parasites present was counted by microscopy and N-acetylglucosamine was added to all cultures to specifically kill asexual parasites. On Day 9, when gametocytes developed enough that they were readily distinguished from asexual stage parasites by morphology, the number of gametocytes were counted by microscopy. Percentage sexual conversion was calculated by dividing this by the proportion of parasite-infected red blood cells on Day 3.

AP2-G Polypeptide Expression

AP2-G polypeptide expression was validated using Western blotting and immunofluorescence assays to compare the numbers of cells expressing PfAP2-G in parasites with the mutated pairing element compared with the parental cell line (AP2-G-HA-FKBP).

AP2-G mRNA expression was validated using RT-qPCR to compare the levels of pfap2-g transcript in parasites with the mutated pairing element compared with the parental cell line (AP2-G-HA-FKBP).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A *Plasmodium* parasite, wherein the genome of said *Plasmodium* parasite comprises:

(a) exogenous nucleic acid encoding a destabilization domain fused to the 3' end of nucleic acid encoding an AP2-G polypeptide, and (b) at least one disrupted pairing element, wherein said disrupted pairing element comprises a disruption in a pairing element flanking said nucleic acid encoding said AP2-G polypeptide fused to said nucleic acid encoding said destabilization domain;

wherein said *Plasmodium* parasite, when contacted with a ligand that stabilizes said destabilization domain, expresses the AP2-G polypeptide and commits to gametocytogenesis.

2. The *Plasmodium* parasite of claim 1, wherein said *Plasmodium* parasite is selected from the group consisting of a *Plasmodium falciparum*, a *P. berghei*, a *P. voelii*, a *P. vivax*, a *P. malariae*, a *P. ovale*, and a *P. knowlesi.*

3. The *Plasmodium* parasite of claim 1, wherein said *Plasmodium* parasite is a *P. falciparum.*

4. The *Plasmodium* parasite of claim 1, wherein said destabilization domain comprises a FKBP destabilization domain.

5. The *Plasmodium* parasite of claim 1, wherein said destabilization domain comprises a glmS ribozyme.

6. The *Plasmodium* parasite of claim 1, wherein said exogenous nucleic acid encoding a destabilization domain comprises nucleic acid encoding a peptide tag.

7. The *Plasmodium* parasite of claim 1, wherein said disrupted pairing element is a 5' pairing element.

8. The *Plasmodium* parasite of claim 1, wherein said disrupted pairing element is a 3' pairing element.

9. The *Plasmodium* parasite of claim 1, wherein the genome of said *Plasmodium* parasite comprises a disrupted 5' pairing element and a disrupted 3' pairing element.

10. A method for generating a sexual stage *Plasmodium* parasite, wherein said method comprises administering a ligand to a *Plasmodium* parasite comprising a regulatable AP2-G polypeptide, wherein the genome of said *Plasmodium* parasite comprises:

(a) exogenous nucleic acid encoding a destabilization domain fused to the 3' end of nucleic acid encoding an AP2-G polypeptide, and (b) at least one disrupted pairing element, wherein said disrupted pairing element comprises a disruption in a pairing element flanking said nucleic acid encoding said AP2-G polypeptide fused to said nucleic acid encoding said destabilization domain;

wherein said ligand stabilizes said destabilization domain, and wherein said stabilization is effective to increase the level of AP2-G polypeptide present within the *Plasmodium* parasite to commit the *Plasmodium* to gametocytogenesis.

11. The method of claim 10, wherein said *Plasmodium* parasite is selected from the group consisting of a *Plasmodium falciparum*, a *P. berghei*, a *P. voelii*, a *P. vivax*, a *P. malariae*, a *P. ovale*, and a *P. knowlesi*.

12. The method of claim 10, wherein said *Plasmodium* parasite is a *P. falciparum*.

13. The method of claim 10, wherein said destabilization domain comprises a FKBP destabilization domain.

14. The method of claim 13, wherein said ligand is a Shield-1 (Shld1) molecule.

15. The method of claim 10, wherein said destabilization domain comprises a glmS ribozyme.

16. The method of claim 15, wherein said ligand is N-acetyl glucosamine.

17. The method of claim 10, wherein said exogenous nucleic acid encoding a destabilization domain comprises nucleic acid encoding a peptide tag.

18. The method of claim 10, wherein said disrupted pairing element is a 5' pairing element.

19. The method of claim 10, wherein said disrupted pairing element is a 3' pairing element.

20. The method of claim 10, wherein the genome of said *Plasmodium* parasite comprises a disrupted 5' pairing element and a disrupted 3' pairing element.

* * * * *

SEQUENCE LISTING

```
<160> NUMBER OF SEQ ID NOS: 5

<210> SEQ ID NO 1
<211> LENGTH: 18
<212> TYPE: DNA
<213> ORGANISM: Plasmodium falciparum

<400> SEQUENCE: 1

tatgtatatg tatatgta                                              18


<210> SEQ ID NO 2
<211> LENGTH: 24
<212> TYPE: DNA
<213> ORGANISM: Plasmodium falciparum

<400> SEQUENCE: 2

tatatgtatg tgtatatgta tgtg                                       24


<210> SEQ ID NO 3
<211> LENGTH: 12
<212> TYPE: DNA
<213> ORGANISM: Plasmodium falciparum

<400> SEQUENCE: 3

trtrkrkrtg kg                                                    12


<210> SEQ ID NO 4
<211> LENGTH: 22
<212> TYPE: DNA
<213> ORGANISM: Artificial
<220> FEATURE:
<223> OTHER INFORMATION: disrupted pairing element

<400> SEQUENCE: 4

tacgtatgtc tacccgtatg tc                                         22


<210> SEQ ID NO 5
<211> LENGTH: 22
<212> TYPE: DNA
<213> ORGANISM: Plasmodium falciparum

<400> SEQUENCE: 5

tatgtatgtg tatatgtatg tg                                         22
```